United States Patent [19]
Nonaka et al.

[11] Patent Number: 4,596,776
[45] Date of Patent: Jun. 24, 1986

[54] PROCESS FOR MAKING STARCH HYDROLYZATES AND HIGH FRUCTOSE SYRUPS

[75] Inventors: Henry H. Nonaka, Orland Park, Ill.; Soichiro Ushiro, Tokyo, Japan

[73] Assignee: CPC International Inc., Englewood Cliffs, N.J.

[21] Appl. No.: 584,370

[22] Filed: Feb. 28, 1984

[51] Int. Cl.$^4$ ............................................. C12D 19/14
[52] U.S. Cl. ...................................... 435/94; 435/96; 435/99
[58] Field of Search ........................ 127/43, 44, 67, 68, 127/69, 70; 435/94, 96, 99

[56] References Cited
U.S. PATENT DOCUMENTS
186,935  2/1877  Johnson .
3,910,820 10/1975 Holt et al. .
4,069,103  1/1978  Muller .

FOREIGN PATENT DOCUMENTS
542387  1/1942  United Kingdom .

OTHER PUBLICATIONS
Tegge, et al., *Starke*, 34, 386–390 (1982).
Van Twisk, *Starke*, 22, 228–230 (1970).
Bos, et al., *Starke*, 26, 181–185 (1974).
Van Twisk, et al., *Starke*, 28, 432–435 (1976).
Knudsen, et al., *Starke*, 21, 284–291 (1969).

Primary Examiner—Raymond N. Jones
Assistant Examiner—Carolyn Paden

[57] ABSTRACT

An improved process is provided for conversion of crude starch-containing materials such as broken-polished rice and corn grits to starch hydrolyzates and high fructose syrups. The process employs short steeping and milling steps before enzymatic liquefaction and saccharification of the starch. The process causes a minimum solubilization of protein giving readily purified products.

5 Claims, No Drawings

PROCESS FOR MAKING STARCH HYDROLYZATES AND HIGH FRUCTOSE SYRUPS

FIELD OF THE INVENTION

This invention relates to a process for making starch hydrolyzates and high fructose syrups from crude starch-containing materials such as broken polished rice and corn grits.

BACKGROUND OF THE INVENTION

Commercial processes for making starch hydrolyzates usually involve liquefying a slurry of refined starch by means of an alpha-amylase enzyme and, subsequently, subjecting the liquefied product to the action of a saccharifying enzyme such as glucoamylase. The products obtained by this method have a high content of the monosaccharide glucose. The process is of importance because the glucose-containing syrups are useful in their own right as sweeteners and constituents of many food products. The syrups are also useful as intermediates in the production of such products as high fructose syrups.

The starting materials commonly used to prepare starch hydrolyzates are refined starches such as corn starch obtained by the wet milling of the whole corn grain.

There would be a considerable economic advantage if crude starch-containing substances rather than refined starch could be used as the starting material for making starch hydrolyzates. Crude starch materials, such as broken polished rice, are readily available in certain countries as a by-product of the manufacture of polished rice.

Previous attempts to use such unrefined starting materials have met with limited success. Crude starch-containing materials contain associated proteins that are converted to soluble products during the starch hydrolysis. These soluble proteins are difficult to remove and lend undesirable color and taste properties to the final product. These impurities also interfere with the conversion of the starch hydrolyzates to high fructose syrups.

Early attempts to prepare glucose-containing syrups by hydrolysis of rice grains made use of acid hydrolysis of the starch. This acid treatment not only hydrolyzed the starch but hydrolyzed the protein as well giving materials that either could not be purified or which required very costly purification procedures.

More recently, Tegge and Richter proposed a process for the use of sorghum and broken rice as raw materials for the production of glucose (Stärke, 34, 386-390 (1982). They concluded, however, that the products were of lower purity than those obtained using refined starch as the starting material. Even after the products were purified extensively, they were not suitable for conversion to fructose syrup with an immobilized glucose isomerase. A further method (Holt, et al, U.S. Pat. No. 3,910,820) used maize (corn) grits as the source of crude starch. Corn grits are obtained by dry milling corn to remove much of the fiber and oil-bearing material. The process disclosed by Holt, et al included a water tempering of the grits, a liquefaction step followed by an acidification and filtration before the saccharification step was carried out. The protein content of the product was not given, but it was necessary to refine it extensively before it could be converted to a fructose syrup. This process required two additions of alpha-amylase to accomplish the liquefaction, and removal of protein was essential before the saccharification step could be carried out because of protein solubilization during the process.

We have now discovered a process for preparing starch hydrolyzates that causes little solubilization of the protein present in crude starch materials. It can be carried out with the addition of only one portion of alpha-amylase enzyme and does not require a filtration step to remove protein before saccharification.

SUMMARY OF THE INVENTION

Briefly, in accordance with this invention, a process is provided whereby crude starch-containing materials are converted to glucose-containing syrups. The process comprises the steps of:

(a) steeping the crude starch-containing material for from about 2 hours to about 6 hours in a dilute aqueous solution of sulfur dioxide;

(b) washing the product of Step (a) with water to remove water-soluble material;

(c) treating an aqueous slurry of the washed product of Step (b) with an alpha-amylase enzyme for a sufficient time to liquefy the starch in the product; and (d) saccharifying the liquefied starch product of Step (c) with glucoamylase at a pH of about 5.0 to about 6.0 for a sufficient time to obtain the desired amount of glucose in the product.

Additionally, in accordance with this invention, a process is provided whereby crude starch-containing material is converted to a maltose-containing syrup. The process comprises the steps of:

(a) steeping the crude starch-containing material for from about 2 hours to about 6 hours in a dilute aqueous solution of sulfur dioxide;

(b) washing the product of Step (a) with water to remove water-soluble material;

(c) treating an aqueous slurry of the washed product of Step (b) with an alpha-amylase enzyme for a sufficient time to liquefy the starch in the product; and (d) saccharifying the liquefied starch product of Step (c) with malt extract at a pH of about 5.0 to about 6.0 for a sufficient time to obtain the desired amount of maltose in the product.

DETAILED DESCRIPTION OF THE INVENTION

The process of this invention is applicable to cereal grains from which the bulk of the fiber and fat have been removed. It is particularly applicable to broken polished rice. Corn grits from which the bulk of the corn oil has been removed are also suitable for use in this process.

The first step in the process of the present invention involves steeping the broken polished rice or other crude starch-containing material in water containing sulfur dioxide. The sulfur dioxide may be added as a gas or as a solution of sodium bisulfite. Although the amount of sulfur dioxide present is not critical, large concentrations are to be avoided since they tend to produce a color which is hard to remove from the final product. The preferred range of sulfur dioxide is from about 0.05 to about 0.2% by weight of the steepwater used. The pH of the steep solution is preferably in the range of about 5.5 to about 6.2. Use of a lower pH tends to solubilize an undesired amount of the protein and use of a higher pH causes undesired color development in the products. Steeping is carried out at a temperature of from about 45° C. to about 60° C., preferably at about 50° C. Higher temperatures which cause gelatinization of the starch should be avoided. Steeping is carried out for from about 2 hours to about 6 hours, preferably about 4 hours. Longer steeping times can be employed but they tend to solubilize more of the protein associated with the crude starch.

After the crude starch-bearing material has been steeped, it is washed to remove water-soluble material. Either before or after the washing step, the material may be milled to reduce the size of the particles. It is not essential to mill the material before it is liquefied. However, milled material is liquefied more rapidly by enzymes, and it is often necessary to reduce the particle size if the enzymatic liquefaction is to be carried out by means of a steam injection heater. Milling can be accomplished using commercially available milling equipment. A Waring Blendor is suitable for use on a laboratory scale while an Entoleter mill is satisfactory for use on a larger scale.

The washed starch-containing product is liquefied with an alpha-amylase enzyme. Liquefaction conditions will vary with the alpha-amylase employed. It is convenient to use a thermoduric alpha-amylase such as THERMAMYL which exhibits an appreciable degree of stability at 100° C. With this enzyme, the liquefaction is carried out at a pH of about 6.2 in the presence of 100 ppm $Ca^{++}$. From 1 to 2 units of THERMAMYL per gram of the starch-containing material is used. The enzyme is allowed to act on the material for a sufficient time to liquefy substantially all of the starch present. Usually this occurs within 2 hours at 100° C.

The crude liquefied starch is next saccharified using any of the common saccharifying enzymes. If a syrup with a high glucose content is desired, saccharification is carried out with glucoamylase for a sufficient time to convert at least about 95% of the carbohydrate present to glucose. This occurs in about 4 days when the saccharification is carried out at 60° C. in the presence of about 0.1 to 0.2 units of glucoamylase per gram of starch-containing material. In order to obtain a product with low protein content, the saccharification should be carried out at a higher pH than is conventionally done with glucoamylase. We have discovered that if the pH of the medium is maintained in the range of about 5.0 to about 6.0, rather than at the conventional pH of about 4, saccharification proceeds at a satisfactory rate and very little of the protein is solubilized. This is an important discovery of the present process leading to glucose-containing syrups that filter rapidly and are readily purified because of their low soluble protein content. The liquefied starch produced by the process of this invention can also be converted to high maltose syrups by the use of a malt enzyme in place of glucoamylase.

The syrups produced by the process of this invention can be purified by conventional means, such as treatment with carbon and ion-exchange resins. Furthermore, such purified material with a high glucose content is suitable for conversion to fructose-containing syrups by means of immobilized glucose isomerase enzyme. The products of this invention do not inactivate the glucose isomerase enzyme as did the syrups obtained by the prior processes from broken polished rice.

The process of this invention is illustrated further by the following examples in which all parts and proportions are by weight unless otherwise specified. The protein values reported were obtained by multiplying the percent nitrogen determined by Kjeldahl analysis by a factor of 5.95. The reported ash values were obtained by combustion of the samples after addition of sulfuric acid. Samples of the hydrolyzed starch were analyzed for carbohydrate content by high performance liquid chromatography in accordance with the following technique. Components were chromatographed by elution with water from a cation-exchange resin in the calcium form. The eluted components were detected by means of a differential refractometer. All carbohydrates were quantitated using an electronic integrator. The general procedure is that given in "Analysis of Carbohydrate Mixtures by Liquid Chromatography", Am. Soc. Brew. Chem. Proc., 1973, pp. 43-46. The column used is HPX-87 in the calcium form, Bio-Rad Laboratories, Richmond, California.

Units of alpha-amylase activity are determined as follows:

The solution to be analyzed is diluted with 0.0025 M calcium chloride solution to give a final concentration of about 0.25 unit of activity per ml. One ml of properly diluted enzyme solution is added to 10 ml of a 1% soluble starch solution containing 0.03 M acetic acid buffer (pH 6.0) and 0.03 M. calcium chloride. The reaction is carried out for 10 minutes at 60° C. One ml of the reaction solution is put in a 100-ml graduated flask containing 50 ml of 0.02 N hydrochloric acid, and after adding 3 ml of 0.05% iodine solution thereto, the total volume is made up to 100 ml by the addition of water. The blue color which develops is measured for absorbance at 620 nm. The amount of the enzyme required to decompose 10 mg/starch in 1 minute is defined as 1 unit.

$$1 \text{ unit} = \frac{D_o - D_s}{D_o} \times \frac{50}{10 \times 10} \times \text{(dilution factor)}$$

where, $D_o$=absorbance of control solution (water is added instead of the enzyme solution)

$D_s$=absorbance of the reaction solution

Glucoamylase activity units are determined as follows:

The substrate is a 10–20 D.E. alpha-amylase thinned hydrolyzate of waxy maize starch dissolved in water and diluted to 4.0 grams of dry substance per 100 ml of solution. Exactly 50 ml of the solution is pipetted into a 100-ml volumetric flask. To the flask is added 5.0 ml of 1.0 molar sodium acetate-acetic acid buffer (pH 4.3). The flask is placed in a water bath at 60° C. and after 10 minutes the proper amount of enzyme preparation is added. At exactly 120 minutes after addition of the enzyme preparation, the solution is adjusted to a phenolphthalein end point with 0.5 N sodium hydroxide. The solution is then cooled to room temperature and diluted to volume. A reducing sugar value, calculated as dextrose, is determined on the diluted sample and on a control with no enzyme preparation added. Glucoamylase activity is calculated as follows:

$A = (S-B)/(2 \times E)$ where,

A = glucoamylase activity units per ml (or per gram) of enzyme preparation
S = reducing sugars in enzyme converted sample, grams per 100 ml
B = reducing sugars in control, grams per 100 ml
E = amount of enzyme preparation used, ml (or grams)

S should not exceed 10 grams per 100 ml.

EXAMPLE 1

Broken polished rice obtained from Pakistan was slurried with hot water (50° C.), containing 1.52 g/l of NaHSO$_3$. Sufficient rice was used to give a slurry containing 30% rice on a dry solids basis. The mixture was allowed to stand for 4 hours at 50° C. at a pH from 5.7 to 6.1. The slurry was then ground in a 1-gallon Waring Blendor for 60 seconds at the low speed setting. The solid was collected on a filter and washed with distilled water. The washed solid was reslurried in sufficient distilled water to give a slurry containing 30% solids. This slurry was then warmed to 60° C. and the pH was adjusted to 6.2 with 1 M Na$_2$CO$_3$. Sufficient dilute CaCl$_2$ solution was added to give a concentration of 100 ppm dry basis of calcium and 1 unit of alpha-amylase per gram of original dry substance was added. The alpha-amylase employed was THERMAMYL, an alpha-amylase enzyme from *Bacillus licheniformis* available from Novo Laboratories, Wilton, Connecticut. Liquefaction was conducted with vigorous stirring for 2 hours in a boiling water bath. Distilled water was added to replace water lost by evaporation. The hydrolyzate was then cooled to 60° C., and the pH was adjusted to 5.5 with 1 N HCl. Glucoamylase was added at a dosage of 0.14 units per gram of dry substance based on the original dry substance used and saccharification was conducted for 96 hours at 60° C. The glucoamylase used was a commercial glucoamylase produced by *Aspergillus niger* available as G-ZYME from the Enzyme Development Company, 2 Penn Plaza, New York, N.Y. When saccharification was complete, the syrup was filtered to remove solid, and the solid was washed with a small amount of distilled water. The combined filtrate and washings contained 95% dry basis of dextrose, 0.28% dry basis protein and 0.24% dry basis ash.

In a comparative test, the above procedure was followed except that the saccharification was run at pH 4.3, a pH commonly used for saccharification with glucoamylase. The protein content of the hydrolyzate was 1.14% and the ash content was 0.35%. Since such a product contains much more soluble protein, it is harder to purify.

EXAMPLE 2

The general procedure of Example 1 was followed except that commercial corn grits were substituted for broken polished rice. The corn grits used were yellow corn snack meal (Sunlight TM) produced by the J. R. Short Milling Company, Kankakee, Illinois. The syrup obtained by this process contained on a dry solids basis 95.7% glucose, 0.22% protein and 0.22% ash. In a comparable run, except that the saccharification was run at the conventional pH of 4.3, the amount of protein was 0.44% and ash was 0.30%. This example again illustrates the surprisingly low amount of soluble protein retained in the syrup produced from a crude starch raw material when the saccharification step is carried out at the pH of about 5.5.

EXAMPLE 3

The procedure of Example 1 was followed except that in the saccharification step the glucoamylase was replaced with malt extract added to give a malt level of 0.12% on a dry solids basis. The malt extract used was Enzeco Malt Extract, 400 Lintner, available from the Enzyme Development Company, 2 Penn Plaza, New York, N.Y. After 72 hours saccharification at pH 5.1, there was obtained a high maltose syrup containing on a dry substance basis 57.6% maltose, 2.8% glucose, 15.6% maltotriose and 24.0% of higher oligosaccharides. Protein and ash contents were both below 0.3%.

EXAMPLE 4

Preparation of a dextrose hydrolyzate from broken polished rice was conducted on a pilot plant scale in the following manner. Broken polished rice was steeped in a solution containing an initial concentration of between 800 and 1000 ppm of SO$_2$. Steeping was accomplished by adding sufficient steepwater to cover the rice and then warming it to 49° C. The steepwater was circulated through the rice by means of a pump for 4 hours before it was removed and the steeped rice was washed with an additional volume of water. The steeped rice slurried in a volume of fresh water was milled by passing it through a 68.6 cm diameter centrifugal mill, Type FM, manufactured by the Entoleter Division of Safety Railway Service Corp., New Haven, Connecticut. The coarser particles in the slurry were scalped off with a 0.249×0.686 mm Rotex screen, Model 11, manufactured by Rotex, Inc., Cincinnati, Ohio, and remilled through the Entoleter mill. The finely screened slurry was then delivered to the liquefaction system. The milled rice slurry was mixed with 2 units of THERMAMYL alpha-amylase per gram of rice, the pH was adjusted to 6.2 and CaCl$_2$ was added to give a calcium concentration of 100 ppm. The mixture was passed through a steam injection heater, heated by direct steam injection to a temperature of 106° C. to 108° C., and held for 6 minutes at this temperature. The mixture containing the alpha-amylase was then held in a tank for 90 minutes at 96° C. to 98° C. The pH was adjusted to 5.5 and 0.18 unit of glucoamylase enzyme was added per gram of solid. Saccharification with the glucoamylase was conducted at 60° C. for 4 days. The hydrolyzate was filtered through a 0.5 m$^2$ rotary vacuum filter (manufactured by Ametek, Inc., Temecula, California) using a diatomaceous earth precoat and decolorized by passing through activated carbon (Darco S-51). The syrup contained, on a dry solids basis, 90% glucose, 0.30% protein, and 0.24% ash.

EXAMPLE 5

A hydrolyzate prepared in Example 4 was converted to a fructose-containing syrup by the following process. The hydrolyzate was first concentrated by evaporation under reduced pressure to give a 55% solution. It was then double pass ion exchanged using Duolite C-25D and Dow XFS-4066 resins. The pH of the solution was adjusted to 8.5, 100 ppm dry basis of Mg$^{++}$ was added and the material was passed through a column containing immobilized glucose isomerase. The flow rate was adjusted to give a syrup in which 42% of the carbohydrate was fructose. Isomerization was conducted continuously for 10 days with only a slight reduction in the activity of the isomerase enzyme occurring during that time. This demonstrates that the glucose syrup obtained by the process of this invention is suitable for conversion to fructose syrup using an immobilized glucose isomerase enzyme.

Thus, it is apparent that there has been provided, in accordance with the invention, an improved process for the production of starch hydrolyzates and high fructose syrups from crude starch-containing materials. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the preparation of a glucose-containing syrup from broken polished rice which comprises the steps of:
   (a) steeping the broken polished rice for from about 2 hours to about 6 hours in a dilute aqueous solution of sulfur dioxide;
   (b) washing the product of Step (a) with water to remove water-soluble material;
   (c) treating an aqueous slurry of the washed product of Step (b) with an alpha-amylase enzyme for a sufficient time to liquefy the starch in the product; and
   (d) saccharifying the liquefied starch product of Step (c) with glucoamylase at a pH of about 5.0 to about 6.0 for a sufficient time to obtain the desired amount of glucose in the product.

2. The process of claim 1 wherein the product of Step (a) is milled before it is washed.

3. The process of claim 1 wherein the washed product of Step (b) is milled before it is treated with alpha-amylase.

4. The process of claim 1 wherein saccharification is carried out for a sufficient time until glucose comprises at least about 95% by weight of the carbohydrates present in the product.

5. The process of claim 4 wherein the glucose-containing product is further treated with glucose isomerase enzyme to give a syrup in which at least about 40% by weight of the carbohydrate present is fructose.

* * * * *